(12) United States Patent
Fleming

(10) Patent No.: US 7,284,434 B1
(45) Date of Patent: Oct. 23, 2007

(54) RIGID-CONTACT DRIPLESS BUBBLER (RCDB) APPARATUS FOR ACOUSTIC INSPECTION OF A WORKPIECE IN ARBITRARY SCANNING ORIENTATIONS

(76) Inventor: Marvin F. Fleming, 3307 Sahalee Way NE., Sammamish, WA (US) 98074

( * ) Notice: Subject to any disclaimer, the term of this patent is extended or adjusted under 35 U.S.C. 154(b) by 0 days.

(21) Appl. No.: 10/980,420

(22) Filed: Nov. 2, 2004

(51) Int. Cl.
  *G01N 29/28* (2006.01)
(52) U.S. Cl. .................................................. 73/644
(58) Field of Classification Search ................ 73/644, 73/620
  See application file for complete search history.

(56) References Cited

U.S. PATENT DOCUMENTS 5,469,744 A * 11/1995 Patton et al. ................. 73/644
6,298,727 B1 * 10/2001 Fleming et al. ............... 73/644
7,021,143 B2 * 4/2006 Dasch ......................... 73/620

* cited by examiner

*Primary Examiner*—John E. Chapman
(74) *Attorney, Agent, or Firm*—Allston L. Jones

(57) ABSTRACT

A lightweight apparatus for performing ultrasonic immersion inspection of a workpiece in an arbitrary orientation that uses significantly less couplant and has a reduced footprint size while providing ultrasonic performance levels comparable to those typically reached using immersion tanks, bubblers, or Dripless Bubblers™ while accommodating large and small ultrasonic beamwidths. The apparatus can be used with manual, automated, or electronic scanning techniques. The apparatus provides a quickly enabled ultrasonic coupling means that minimizes the area of the part wetted, and also can recover spent couplant. As a result, this reduces the number and type of contaminates to which the workpiece is exposed when used when compared to prior art immersion tanks and bubblers.

9 Claims, 3 Drawing Sheets

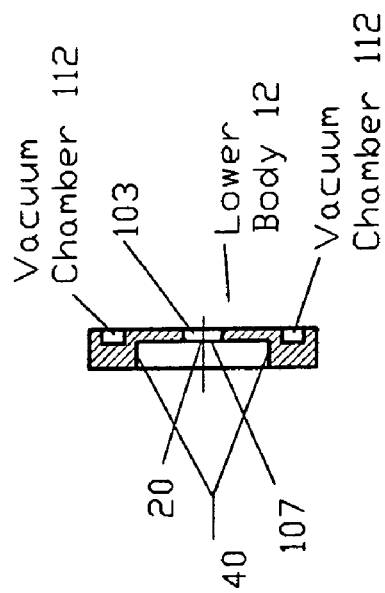
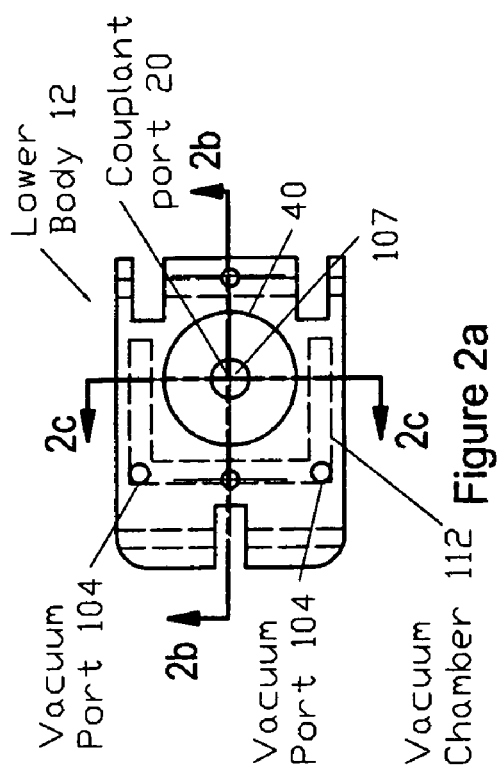
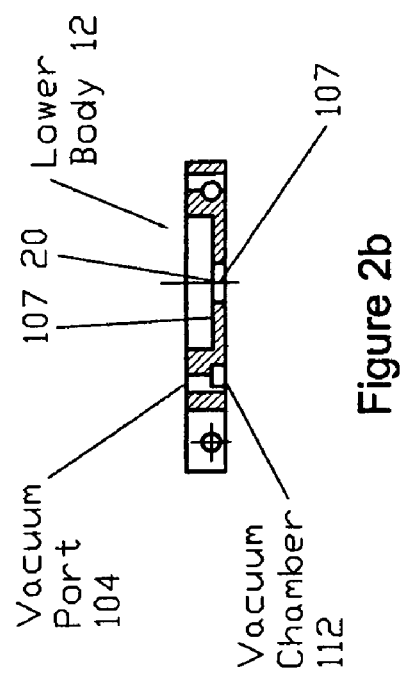

RIGID-CONTACT DRIPLESS BUBBLER (RCDB) APPARATUS FOR ACOUSTIC INSPECTION OF A WORKPIECE IN ARBITRARY SCANNING ORIENTATIONS

BACKGROUND OF THE INVENTION

1. Field of the Invention

An acoustic inspection device, namely one that has a small footprint, exposes the workpiece to few contaminants, rapidly establishing coupling with the workpiece, requires less couplant than earlier devices, and a small localized couplant chamber to wet the workpiece without placement in an immersion bath.

2. Description of the Prior Art

Nondestructive Inspection (NDI) determines the quality of a workpiece without causing damage to the workpiece. One prior art NDI technique uses acoustic waves to inspect a workpiece: this technique directs an incident acoustic wave at a workpiece and analyzes the reflection to determine the workpiece's quality. Acoustic inspection is helpful, for example, to determine the integrity of airplane components including the wing, fuselage and empennage by detecting disbanded lap-splices, corroded rivet joints, and similar structural defects. Acoustic inspection is also helpful, for example, to determine the integrity of automobile, electronic, and microelectromechanical systems (MEMS) components, including resistance spot and line welds by detecting unsatisfactory spot welds, disbonded lap splices, butt welded joints, and similar joining techniques using a wide variety of materials and surface finishes including high strength steels, aluminum, plastics, ceramics, and composites.

A typical apparatus for acoustically inspecting a workpiece includes a pulse generator electrically connected to a transducer assembly that generates a focused acoustic wave. The acoustic wave travels through a transmission medium and onto the workpiece. Acoustic reflections from the workpiece radiate back to the transducer and cause the transducer to generate a corresponding electrical signal. An operator or a computer processor then analyzes the electrical signal to determine the quality of the workpiece.

Ultrasonic NDI, in particular, can improve the inspection spatial resolution and the signal to noise by using a focused acoustic beam that may be focused by electronic or ultrasonic lenses. It is noteworthy that even so-called flat-focused transducers exhibit a natural focus that may or may not be used as a focused transducer. Also, mechanical or electronic scanning methods may be used to cause the ultrasonic beam to scan over the workpiece. In all of these cases, Ultrasonic NDI requires quality and reliable acoustic coupling without introducing spurious signals; and, the effectiveness of any given technique can be compared for reference purposes to the performance of a similar transducer used in a water immersion mode.

Known related inspection apparatus are described by Fleming in the U.S. Pat. No. 6,298,727 and Patton in the U.S. Pat. No. 5,469,744 uses an acoustic apparatus called a Contact Adaptive Bubbler (CAB). These CABs consist of a tubular member containing an ultrasonic transducer, a couplant chamber, and a couplant reservoir between the transducer and the workpiece. A membrane that generally avoids contact with the workpiece is used to separate the couplant chamber and the couplant reservoir. Couplant is continuously supplied to replenish couplant leaks. A vacuum chamber recovers couplant that leaks from the couplant reservoir.

However, in practice, it has been found that CAB devices are too large in overall size and footprint and too costly for many applications. Attempts to reduce CAB size have introduced ultrasonic signal attenuation, unwanted or spurious signals and unreliable ultrasonic coupling. Additionally, in some applications, large size hoses are required for both the couplant supply and the vacuum couplant recovery lines to the CABs; these large lines create undesirable forces that easily disturb the orientation of the CAB device relative to the workpiece. Additionally, larger CAB footprints limit their use near surface obstructions and near workpiece edges where ultrasonic coupling is lost. Finally, the larger CAB devices require larger couplant supplies and ancillary equipment, thereby restricting applications and portability.

What is needed is a smaller CAB device that provides reliable ultrasonic coupling. Such a CAB device needs to have a small size and a small footprint, require small amounts of couplant and vacuum, and adapts to manual and automated scanning techniques. The present invention provides such a smaller CAB device.

SUMMARY OF THE INVENTION

The present invention provides an apparatus and method for acoustically inspecting a workpiece without having to immerse the workpiece. For purposes of the discussion, the present invention is called a rigid contact, dripless bubbler (RCDB). The RCDB is used to reliably generate ultrasonic data in the form of A-scans, B-scans, C-scans or other form of ultrasonic data useful in component evaluations. The methods of the present invention include steps for performing the invention.

The present invention provides an RCDB that can accommodate uneven workpiece surfaces while providing reliable and distortion-free acoustic coupling comparable to coupling accomplished in an immersion tank independent of the orientation of the workpiece being inspected.

The RCDB provides ultrasonic coupling that accommodates larger ultrasonic beams in a smaller RCDB package, with a smaller footprint.

The RCDB provides a means of ultrasonic coupling that accommodates larger ultrasonic beams in a smaller RCDB package; without introducing either significant signal distortion or excessive signal attenuation compared to operation of the same ultrasonic transducer in an immersion tank.

The RCDB provides a means of ultrasonic coupling on surfaces having unevenness (such as encountered on workpieces containing spot welds having 1-2 mm height variations) and that disturb the desired orientation of the RCDB to a tolerable extent as it passes over the rough areas.

Additionally, the RCDB provides a means for supplying reliable ultrasonic coupling, eliminating debris and bubbles attached to the workpiece surface that can spoil the quality of the ultrasonic coupling.

The RCDB invention increases the orientation accuracy for scanning uneven surfaces by using improved distribution of the couplant and vacuum in their respective chambers. As a result, the invention uses a smaller diameter, shorter hose lengths in the RCDB for couplant supply, and recovery to reduce hose disturbance forces and the resultant mis-orientation.

The present invention can be used on smooth or patterned surfaces (having unevenness as a normal feature of the workpiece, such as an electrostatic chuck) where the flow and surface tension of the couplant is used in conjunction with the location, shape and size of the couplant feed and recovery chambers to accomplish reliable acoustic coupling.

In some cases, the bearing surface of the RCDB may or may not be in direct contact with the workpiece surface (e. g.: The present invention could be used in a standard immersion tank with and without contacting the workpiece to avoid filling the tank with couplant and thereby avoiding immersion of the workpiece).

Another feature of the present invention is an RCDB that uses less couplant. This is accomplished by using smaller couplant chambers, producing more efficient dispersion of the couplant, minimizing surface air being pulled under the RCDB, and turning off the couplant flow when the RCDB is not needed. The turning off of the couplant flow requires anti-siphon and anti-drain features, which are included in the RCDB couplant chamber design.

Another object of the present invention is to provide an RCDB with more flexible vacuum supply lines to accomplish more accurate orientation of the RCDB to the workpiece; when the RCDB is used in direct contact with the workpiece. The couplant and vacuum supply lines can provide disturbance forces preventing the RCDB from accurately aligning to the workpiece surface by pressing uniformly against the workpiece surface. This is accomplished through the use of smaller diameter lines for the couplant and vacuum supply lines.

The invention provides a reduced footprint of the RCDB. This is accomplished through the use of smaller transducers, smaller bearing surfaces, and smaller diameter lines for the couplant and vacuum supply lines.

BRIEF DESCRIPTION OF THE FIGURES

FIG. 2a is a top view of the lower body of the acoustic inspection device of FIG. 1;

FIG. 2b is a cross-sectional view of FIG. 2a taken along line 2b-2b;

FIG. 2c is a cross-sectional view of FIG. 2a taken alone line 2c-2c; and

DESCRIPTION OF THE PREFERRED EMBODIMENT

The present invention is an acoustic inspection device, namely one that includes a small localized couplant chamber (smaller than the prior art) to wet the workpiece, eliminating the need to place the workpiece in an immersion bath. Additionally, the present invention has a small footprint, exposes the workpiece to less contaminants than prior art devices, provides rapid coupling to the workpiece and requires less couplant than prior art devices. These features overcome the shortcomings of a full range of prior art ultrasonic transducers that normally require complete or partial immersion of the workpiece during examination and scanning operations.

The following description is provided for a preferred embodiment of the present invention. Those skilled in the art will appreciate that various changes and modifications can be made to the discussed preferred embodiment while remaining within the scope of the present invention.

That embodiment of the present invention is described in relation to the included figures. As will be seen from the following discussion, the acoustic inspection device of the present invention can accurately be referred to as a rigid contact, dripless bubbler (RCDB).

Figure 1:
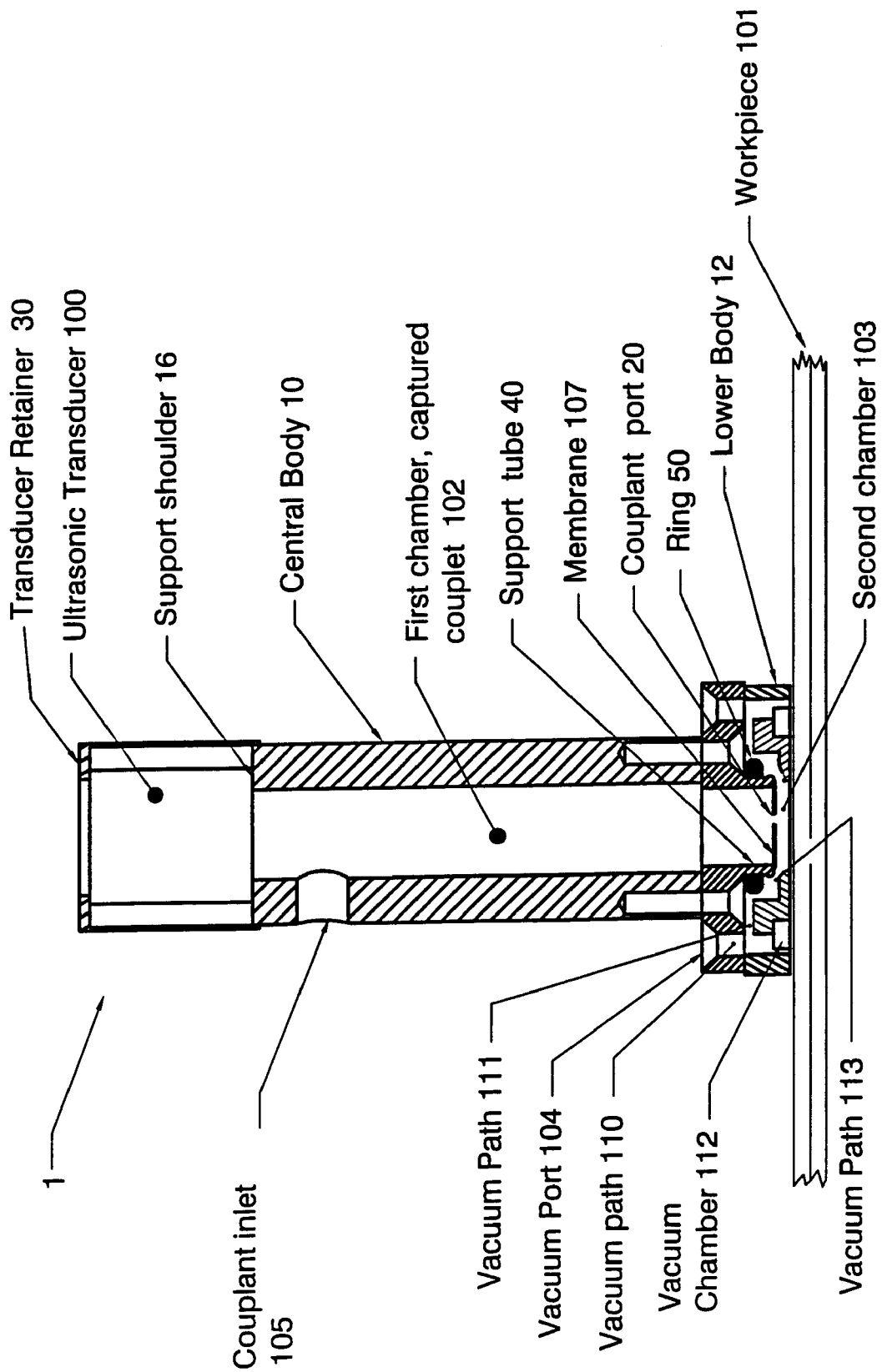
FIG. 1 is a vertical cross section of the acoustic inspection device of the present invention.

FIG. 1 shows a vertical cross section of an acoustic inspection device 1 of the present invention that has a central body 10 that is attached to a lower body 12. Central body 10 defines a first chamber 102 therewithin. At the proximate end of central body 10, and internal to first chamber 102, ultrasonic transducer 100 is mounted between support shoulder 16 and transducer retainer 30 that is attached to the proximate end of central body 10. Central body 10, support shoulder 16 and transducer retainer 30 are each sized and shaped to receive and retain ultrasonic transducer 100 at the proximate end of central body 10. The distal end of central body 10 mates with the proximate end of lower body 12 that defines therein support tube 40 that is in axial alignment with first chamber 102 in central body 10, thus extending the first chamber into lower body 12. Spaced apart from the distal end of lower body 12, within and attached to the side surface of support tube 40, is membrane 107. The space within support tube 40, and between membrane 107 and the distal end of lower body 12 is second chamber 103 with workpiece 101 in contact with the distal end of lower body 12. Thus, membrane 107 serves to separate first chamber 102 from second chamber 103, with second chamber 103 defined by membrane 107, support tube 40 and workpiece 101.

Given this configuration, ultrasonic transducer 100 is, when in place, properly positioned relative to membrane 107 in support tube 40 and workpiece 101, as is appropriate for the particular ultrasonic inspection objectives of the invention. It would be obvious to those skilled in the art that there are other useful arrangements of the ultrasonic transducer 100 relative to the workpiece 101 and the membrane 107.

Additionally, central body 10 defines a couplant inlet 105 through the side thereof into first chamber 102 and membrane 107 defines therethrough at least one couplant port 20 (for convenience, only one couplant port 20 is shown in FIG. 1). Membrane 107 is thin (e.g., latex less than 0.01 inches thick that introduces ultrasonic signal attenuation that is less than 1 dB for frequencies below 25 mHz) sealing the distal end of first chamber 102 to retain couplant therein and to supply couplant to second chamber 103 as further described below through couplant port(s) 20.

Central body 10 and lower body 12 may be fabricated to include several parts, such as support shoulder 16, transducer retainer 30, support tube 40, ring 50, etc. to facilitate easy manufacture, assembly, and repair.

When in use, first chamber 102 is filled, and continuously supplied, with couplant fluid via couplant inlet 105 from an external couplant reservoir (not shown). Air bubbles can be bled (expunged) from first chamber 102 by orienting the inspection device to allow the air to vent via couplant port(s) 20. Couplant port(s) 20 are defined to be sufficiently small so that the surface tension of the couplant adjacent and within the port prevents air from re-entering first chamber 102 when couplant is flowing through port(s) 20 at a normal operational rate, at intermediate rates or completely stopped.

Defined within lower body 12 is vacuum path 110 that opens through the distal face of lower body 12 with a plurality of vacuum paths 110 spaced radially outward from the distal end of second chamber 103 near the outer edge of lower body 12. Alternatively, multiple vacuum ports 104 and direct vacuum paths 110 can be connected to the vacuum chamber 112. Lower body 12 also defines a vacuum port 104 that opens away from workpiece 101 and is in communication with vacuum path 110. Vacuum port 104, when acoustic inspection device 1 is in use, is coupled via a flexible hose (e.g., polyurethane hose with 0.060 to 0.25 inch outer diameter) (not shown) to a vacuum pump (not shown) that is located away from acoustic inspection device 1 to substantially remove excess couplant from the surface of workpiece 101 during inspection while drawing couplant through port(s) 20 in membrane 107 onto workpiece 101 at the point of inspection.

While only one vacuum port 104 is shown in FIG. 1, additional vacuum ports can be provided as necessary to allow for the use of multiple, small diameter flexible hoses that are each, and are collectively, more flexible than a single larger diameter vacuum hose. Couplants used are not compressible; thus couplant is supplied at a rate into couplant inlet 105 and via couplant port 20 that is adjusted to continuously to keep second chamber 103 filled during use. (Note: the use of flexible hoses supports a practical assumption of the couplant being uncompressible). The strength of the vacuum needed is adjusted to accomplish complete, or, nearly complete, recovery of couplant and not necessary to draw couplant through couplant port(s) 20 in membrane 107. Additional vacuum ports 104 and sizes and shapes of vacuum chamber 112 can be used to accomplish a more complete recovery of the couplant. It has been observed that the use of multiple smaller diameter flexible hoses, as opposed to a single larger diameter hose, greatly improves the ability of acoustic inspection device 1 to remain in contact with workpiece 101 while mechanically using the acoustic inspection device 1.

At least one couplant port 20 opens through the membrane 107 to supply couplant to the second chamber 103. Each couplant port 20 has a small diameter (e.g., 0.5 mm) that will prevent air from entering first chamber 102 when couplant flow has stopped but has not reversed. Couplant flows to second chamber 103, directly via couplant port(s) 20, from first chamber 102 and couplant inlet 105 that is connected to a couplant supply source (not shown) through a flexible hose (not shown) (of a similar material and size as the vacuum hose discussed above) with the couplant source located away from acoustic inspection device 1. While only one couplant inlet 105 is shown in FIG. 1, additional couplant inlets 105 could be provided as necessary to permit the use of multiple small diameter flexible hoses that have the beneficial effect of more uniformly reducing and equalizing disturbance forces caused by the hose(s) as the orientation of acoustic inspection device 1 varies relative to the surface of workpiece 101.

The route and flow of couplant through acoustic inspection device 1 is as follows. First chamber 102 is normally filled with couplant and is maintained filled with couplant from an external source received through couplant inlet 105 thus maintaining couplant in contact with membrane 107 with the couplant disposed to pass through couplant port(s) 20 into second chamber 103 to workpiece 101. Second chamber 103 must be maintained full in order to produce the level of ultrasonic coupling desired in the presence of surface debris and bubbles that become attached to the workpiece 101. In numerous tests of the present invention it has been found that properly directed couplant flow into second chamber 103 will sweep debris and bubbles away from the center of the second chamber 103 and thus maintain a complete and unobstructed path for the ultrasonic beam from transducer 100, through the first and second chambers to the surface of the workpiece. To deliver uncompressible couplant substantially at the center of second chamber 103, couplant port(s) 20 are located at or near the center of membrane 107 resulting in a flow of couplant that rapidly and efficiently sweeps bubbles and debris along the surface of the workpiece ahead and away from second chamber 103. This is accomplished by the design of lower body 12 wherein second chamber 103 is connected to vacuum path 110 through vacuum path 113, that is open to second chamber 103, the space around the ring 50 and vacuum path 111. This configuration allows the vacuum to remove air bubbles that might become trapped below membrane 107 and at the top of second chamber 103. Lower body 12 is also configured vacuum debris from the surface of the workpiece in the region of the point of inspection. This is accomplished by vacuum chamber 112 removing material from under lower body 12 the acoustic inspection device is advanced along the surface of the workpiece. That debris is drawn into vacuum chamber 112 and through vacuum path 110 by the vacuum that is applied to vacuum port 104, thus removing surface material before it might become lodged in second chamber 103 while the acoustic inspection device 1 is used to scan a workpiece.

It should be noted that the vacuum is able to perform as it does by the direction and velocity of couplant flow from first chamber 102 into second chamber 103 with the couplant flow continuing whether or not a vacuum is applied. Stated another way, a vacuum Is not necessary for the acoustic inspection device 1 to inspect the surface of a workpiece. The vacuum is an additional feature that aids in that operation by removal of air bubbles and debris, however there are other techniques that can be used to accomplish the removal of air bubbles and debris. The location of small couplant port(s) 20 in the center of membrane 107 facilitates relying on the surface tension of the couplant in couplant port(s) 20 to seal first chamber 102 when couplant flow ceases; thereby preventing release of couplant from first chamber 102 when the acoustic inspection device is not in use. In tests of a prototype of the present invention it has been observed that the acoustic inspection device 1 consumes less than 1 cc of couplant/sec. while providing less than 1 dB loss in the ultrasonic pitch-catch mode of operation and does not create any extraneous ultrasonic signals above 40 dB when compared to immersion testing responses with a membrane at the same location in the beam. This is less by a factor of at least ten, and possibly 100 (application dependant), than that used in the prior art inspection device disclosed in U.S. Pat. No. 6,298,727.

First chamber 102, couplant inlet 105, couplant port(s) 20 and second chamber 103 are supplied by couplant from a couplant supply source (not shown) through a flexible hose (not shown). First chamber 102 and second chamber 103 have a complimentary ultrasonic role, are filled with couplant, and accomplish the same ultrasonic coupling between ultrasonic transducer 100 and workpiece 101 as is accomplished in an immersion tank with the same transducer and workpiece. Second chamber 103 is a couplant reservoir that is designed to be as small as practical that is easily and rapidly replenished by couplant as variations in the workpiece 101 surface are encountered in order to make and retain coupling of the ultrasonic signal and the workpiece.

The width (diameter) of each of first chamber 102 and second chamber 103 is usually larger than the extent of the ultrasonic beam from ultrasonic transducer 100 at any point within the ultrasonic beam to not distort or attenuate the ultrasonic beam and to avoid introduction of spurious ultrasonic signal returns. The ultrasonic beam formed by ultrasonic transducer 100 often forms a horizontal circle in the first and second chambers. In the case where the ultrasonic beam is asymmetric (non circular in the horizontal cross section), the shape of the first chamber 102 and the second chamber 103 are asymmetric to match, in order to transmit the ultrasonic beam with minimum distortion and minimum attenuation.

As a result of the efficient flow of couplant, the width (diameter) of first chamber 102 and second chamber 103 can be relatively large compared to the ultrasonic beamwidth. However, the size of the first chamber 102 and second chamber 103 is to be as small as possible in the horizontal plane simply to minimize the overall size of the acoustic inspection device 1. This coupling arrangement allows the transducer to have a large beamwidth; namely allowing the use of ultrasonic transducers to be focused electronically, with lenses and/or to be scanned.

As mentioned earlier, in operation the acoustic inspection device 1 is used to ultrasonically inspect a workpiece 101 without having to immerse portions of the workpiece 101. Ultrasonic transducer 100 generates an acoustic wave that travels through the coupling fluid disposed in first chamber 102 and second chamber 103 and membrane 107 to strike workpiece 101. The acoustic wave is reflected from workpiece 101, received by ultrasonic transducer 100 (using what is commonly called pulse-echo or pitch catch modes) and a corresponding electrical signal generated by the transducer is processed for evaluation by typical electronics (not shown) that receives the signal from transducer 100.

Two applications for acoustic inspection device 1 are foreseen, contact and close contact. Contact applications are those where the bearing materials used in constructing lower body 12 are placed in contact with the workpiece 101 to properly orient acoustic inspection device 1; close contact applications are where the orientation location of acoustic inspection device 1 is controlled by a scanner (not shown) that transports the acoustic inspection device across a workpiece. In the contact case, bearing materials, such as urethane, brushes, or hardened steel are used to construct lower body 12 both to space membrane 107 from (above) workpiece 101 and to orient the acoustic inspection device 1 relative to the surface of workpiece 101. As the materials used in the construction of the bearing surface of lower body 12 do not precisely follow uneven surfaces on workpiece 101, couplant leaks are re-supplied in order for second chamber 103 to be continuously full. Advantage is taken to use the couplant surface tension to maintain ultrasonic coupling as second chamber 103 passes over a workpiece 101 having uneven or raised surfaces. In the second application, the close contact case—where the scanner controls the orientation and location of the acoustic inspection device 1, the couplant flow and surface tension bridges the gap between lower body 12 and workpiece 101 and accomplishes continuous ultrasonic coupling to the workpiece 101 as the workpiece is evaluated, even in the presence of rough surfaces (typically 1 mm gap and having surface pits of up to 2.5 mm depth with a diameter of 8.9 mm).

Figure 3:
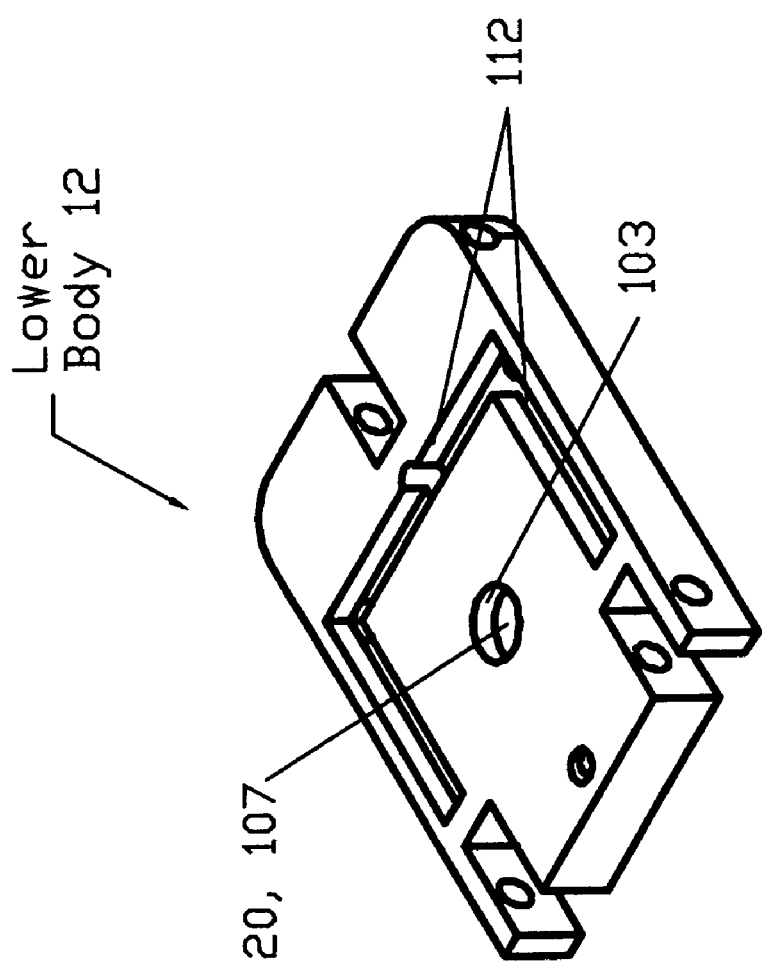
FIG. 3 is a bottom perspective view of the lower body of the acoustic inspection device of FIG. 1.

Attention is now also directed to FIGS. 2a-c and 3. FIG. 2a is a top view of lower body 12; FIG. 2b is a cross-sectional view taken along 2b-2b in the top view of FIG. 2a; and FIG. 2c is a cross-sectional view taken along 2c-2c in the top view of FIG. 2a, while FIG. 3 is a bottom perspective view of lower body 12.

A third chamber is the vacuum chamber 112 that is spaced apart from, and surrounds or partially surrounds, the second chamber 103 (as shown in FIG. 3). Vacuum chamber 112 may take the form of a duct formed in the bottom of lower body 12 by machining a grove therein. The duct of vacuum chamber 112 is connected to vacuum port(s) 104 via vacuum path 110, which assures a uniform vacuum distribution for removal of debris from the surface of workpiece 101 and/or recovery of couplant that escapes from second chamber 103.

The vacuum also removes trapped bubbles from second chamber 103 through vacuum paths 111 and 113 and vacuum port(s) 104 as discussed above. Bubbles may result from several sources; bubbles captured during the initial placement of the acoustic inspection device 1 on the workpiece 101; or bubbles that would form on the surface of workpiece 101 as the acoustic inspection device 1 is moved across the workpiece. Since air is lighter than the couplant, the air rises to the top of second chamber 103 and are directed to the upper sides of second chamber 103 by the flow of couplant through the centrally located couplant port(s) 20. Additionally, bubbles on the surface of the workpiece are either prevented from reaching second chamber 103 by the uncompressible flow of couplant along the surface of the workpiece from the second chamber 103 or/and are captured in vacuum chamber 112 from the workpiece before second chamber 103 is advanced to the position where the bubble has formed. It should be noted that the couplant flow rate is adjusted to a rate that is sufficient to maintain second chamber 103 clear of bubbles and third chamber 112 substantially clear of bubbles during scanning taking into consideration the highest scan speeds used in the examination of workpiece.

Another important use of the acoustic inspection device 1 involves the use of semi-rigid, or rigid, bearing materials in the construction of lower body 12, to facilitate sliding across irregular surfaces (the "contact case" as described above). Smooth sliding is useful for manual or automated mechanical scanning inspection schemes—to avoid erratic scanning caused by any surface roughness on workpiece 101. The contact footprint dimensions of the bearing material of lower body 12 that comes into contact with workpiece 101 effects the accuracy of the alignment of acoustic inspection device 1 with the surface of workpiece 101. The smaller the contact footprint dimensions, the more likely that the user can maintain the orientation of the acoustic inspection device 1 in the nominal orientation, as workpiece 101 is scanned: the nominal orientation being defined as the acoustic inspection device sitting on a flat section of the workpiece. In the case for a curved workpiece, the nominal orientation is normal to the workpiece surface 101. Additionally, the size of lower body 12 also effects the efficiency of couplant recovery from the surface of workpiece 101. Hence a compromise is needed to balance the size (diameter) of the lower body and the need to orient the acoustic inspection device 1 to the surface of workpiece 101. A large size of the lower body limits the capability to inspect a workpiece 101 near edges of, or attachments thereto. It is recognized that rougher surfaces generally require larger and/or additional vacuum chambers like vacuum chamber 112 to remove couplant. The use of the bearing materials sufficiently rigid and small to facilitate easy fabrication of lower body 12 by machining or molding can result in significant cost savings. The use of flexible bearing materials is disclosed in U.S. Pat. No. 6,298,727.

The multiple couplant input and vacuum output ports in acoustic inspection devices has been recognized in the prior art (U.S. Pat. No. 6,298,727) as a means for assuring uniform and reliable coupling for the acoustic beam to the workpiece and for couplant removal in any orientation of the workpiece 101. As mentioned earlier, the use of multiple couplant inputs and vacuum port(s) 104 results in (a) increased following accuracy for the apparatus relative to the surface orientation of workpiece 101 and (b) a smaller footprint for the apparatus on workpiece 101. The acoustic inspection device 1 provides an efficient method of maintaining ultrasonic coupling to the workpiece 101, due to the unique location of the couplant port 20 in membrane 107 and the use of the first chamber 102 both as a couplant supply duct and as a captured chamber of couplant. The flow of couplant from couplant port 20 to the vacuum port 104 provides an efficient method of clearing and maintaining second chamber 103 with couplant. These represent several of the salient features of the acoustic inspection device 1 that make it possible to reduce overall size and simplify parts (to the benefit of easier manufacturing, assembly and cost).

The ancillary supplies for couplant and vacuum have been further reduced in size and capacity with a valve to turn off the couplant supply (not shown) to acoustic inspection device 1 whenever it can be determined that acoustic inspection device 1 is not in use. The diameter of couplant port(s) 20 in the membrane 107 are designed to take advantage of the surface tension of the couplant employed. Couplant port 20 diameters are used that are small enough to prevent air from entering first chamber 102 when the couplant flow is stopped. Anti-siphoning of couplant from first chamber 102 is accomplished using the valve in the couplant supply path to positively close the flow of couplant to acoustic inspection device 1. The small diameter couplant ports 20 used also prevent couplant from draining from first chamber 102 when couplant flow has been turned off. Re-establishing ultrasonic coupling requires clearing second chamber 103 of bubbles and debris that is carried out in a timely fashion by making the volume of second chamber 103 small. Practical tests show that ultrasonic coupling can be reliably re-established in less than 100 milliseconds without disrupting the operator's attention. Significantly faster restarts have been demonstrated.

Given all of these improvements over the prior art (U.S. Pat. No. 6,298,727), the footprint, or diameter, of lower body 12 can be smaller than that of the prior art devices. Acoustic inspection device 1 of the present invention can have a footprint, or diameter, on the order of 0.75 inches when a 0.25 inch diameter ultrasonic beam is used, while prior art devices are much larger with only a few having a diameter smaller than 3.125 inches using the same size ultrasonic beam. The height of the lower body is also reduced however the weight of this reduction is not as important as the design of the transducer 100. Proper selection of the transducer 100 has been used to reduce the overall height. Using the techniques described, it is expected that footprint dimensions can be further reduced. Also, as the footprint size is reduced, the volume of second chamber 103 can be reduced and the amount of couplant fluid that is required to maintain ultrasonic coupling reduced. The ancillary requirements for couplant and for vacuum supplies are also reduced, making the entire system more portable.

The construction of acoustic inspection device 1 is largely dependent on the ultrasonic beam and ultrasonic transducer 100 requirements. Unlike Bauer (U.S. Pat. No. 3,832,889), that uses collimated beams, the present invention uses a focused ultrasonic beam to take advantage of the higher gain and higher resolution afforded by a focused beam. It is noteworthy that all ultrasonic transducers have an intrinsic focus; independent of the use of a lens element to focus the ultrasonic beam. In the present invention, the location of couplant port(s) 20 central to the second chamber 103 results in rapid filling, and clearance of bubbles and debris from second chamber 103 so that large diameter ultrasonic beams can be used without beam distortion, attenuation or introduction of spurious signals.

If signal attenuation, beam distortion, and spurious signals are to be avoided, the distal end of chambers 102 and 103 must have diameters that are sufficiently large to pass all, or practically all, of a beam pattern to meet operating requirements and conditions. In development models of the acoustic inspection device of the present invention, the diameter of membrane 107 has been made sufficiently large to avoid obstructing and interfering with the normal immersion ultrasonic beam. This determination being made by comparison of transducer performance in an immersion tank, using the same transducer, test part and setup (thereby eliminating the housing of the acoustic inspection device 1. Ultrasonic beam obstructions and interferences introduce attenuation of return signals (from intended ultrasonic reflections), spurious signals (when compared to immersion testing), and changes to the immersion beamwidth.

The use of a larger diameter membrane 107, a larger diameter of first chamber 102, and a larger diameter of second chamber 103 accomplishes minimizing reflection signal amplitudes (below 40 dB) off the sides of these chambers; these signals are sometimes referred to as multipath signals that reflect off the sides of chambers 102 and 103 and the front surface of workpiece 101, resulting in false (or spurious) signals having the same time-of-flight as signals behind the front surface of workpiece 101. The front surface of workpiece 101 is usually not flat (especially in the regions around weldments). Multi-path signals are considered false and are troublesome since the time-of-flight is variable and can occur at the same time as ultrasonic signals related to the quality of the component being inspected.

FIGS. 2*a-c* and 3 illustrate a lower body 12 design which has a shaped footprint with the cross-sections of FIGS. 2*b* and 2*c* showing details of the vacuum port 104 that connects to vacuum chamber 112. In the illustration example, there are two vacuum ports 104 used to connect to vacuum chamber 112 that is spaced apart and surrounds the couplant port 20 on three sides. This example design for lower body 12 is for scanning in one direction; toward the side without a vacuum chamber (to the left in FIG. 2*a* and to the right in FIG. 3). In this design example the vacuum ports are through-holes, and the vacuum chamber are grooves in the lower body 12. The through-hole centered on the couplant port 20 forms the walls of the second chamber 103. (Note: this design example illustrates how a design can be made having a small diameter in one direction, see the cross-section of FIG. 2*c*, that is useful in scanning as close as possible to an obstruction. At the same time, the dimension of the cross-section of FIG. 2*b* is long by comparison. This is an advantage also in that this is along the direction of scanning and the longer dimension has the advantage of better maintaining the orientation of the acoustic inspection device 1. The rectangular shaped footprint offers the capability to scan close to obstructions and to align to the workpiece 101 more accurately).

The present invention teaches the means and mechanism for simultaneously preserving the beam pattern and coupling requirements for the acoustic inspection device while minimizing the footprint of the acoustic inspection device, as shown in FIGS. 2*a-c* and 3. This is taught using FIGS. 2*a-c* and 3 where the lower body 12 contains a hole diameter to approximately match the inner diameter of support tube 40 and first chamber 102. The hole in lower body 12 is sufficiently large to pass the beam without degradation and the same diameter requirement applies for the chambers 102 and 103. In order to use the minimum footprint, the thickness of the walls of central body 10 and the lower body 12 must be a minimum size as well. Membrane 107 and support tube 40 are also critical to the size of the footprint so prototypes of the acoustic inspection device 1 of the present invention have been produced with thin (less than 0.25 mm) materials consisting of ultrasonic latex, a thin wall (less than 0.25 mm) for the support tube 40, and a thin diameter cross section (less than 0.5 mm) ring 50 used to support and retain membrane 107. The smallest footprint for lower body 12 requires minimum radial dimensions (less than 1 mm) for each of the essential components: the ring 50, the membrane 107 and the support tube 40 be added to the beam diameter. In practice, larger footprints for lower body 12 may be required to accommodate the requirements of the vacuum chamber 112 and the need to properly orient the acoustic inspection device 1 to workpiece 101.

A smaller footprint is accomplished using one of two methods. The first is a disposable unit consisting of a membrane 107 held in place using a pre-form, usually wire or a composite rod to form ring 50. The second is a reusable and field replaceable design where membrane 107 is attached over a short support tube 40 and retained using a circular ring 50, such as a thin o-ring. Both the reusable and disposable schemes allow accurate dimensional control for second chamber 103, the location of couplant ports 20, and the minimum diameter of the lower body 12.

What is claimed is:

1. A dripless acoustic inspection device for a workpiece comprising:
    a housing including:
        a main body portion having a closed proximate end and an open distal end with side walls extending between said proximate and distal ends defining a cavity between said closed proximate end and side walls; and
        a lower body portion having open proximate and distal ends defining a center passage between said proximate and distal ends with the proximate end of the lower body portion affixed to the distal end of said main body portion;
    an ultrasonic transducer captured within said closed proximate end of said main body portion; and
    a flexible membrane across said center passage of the lower body portion in close proximity to, and spaced-apart from said distal end of said lower body portion with said flexible membrane defining at least one substantially centered hole of a selected small size therethrough;
    a first chamber is defined between said ultrasonic transducer and said flexible membrane and a second chamber is defined between said flexible membrane and the distal end of said lower body portion with said second chamber being substantially smaller than said first chamber, with each of said first and second chambers disposed to contain a liquid couplant;
    said main body portion defines a couplant input port through a side wall into said first chamber below said ultrasonic transducer disposed to input, and maintain, couplant in said first chamber and said at least one substantially centered hole in said flexible membrane disposed to pass couplant therethrough to said second chamber from said first chamber; and
    the size of said at least one substantially centered hole in said flexible membrane is large enough to permit couplant to flow therethrough when said couplant is input and small enough such that surface tension of said couplant prevents couplant from flowing from said first chamber into said second chamber when couplant is not input.

2. The dripless acoustic inspection device for a workpiece as in claim 1 wherein said each of said at least one centered hole through said flexible membrane has a diameter of approximately 0.5 mm.

3. The dripless acoustic inspection device for a workpiece as in claim 1 wherein each of said at least one centered hole through said flexible membrane is small enough to prevent air from passing therethrough from said second chamber into said first chamber when couplant is flowing from said first chamber into said second chamber at a normal operational rate or, at intermediate rates or when said couplant is not flowing.

4. A miniature acoustic inspection device for a workpiece comprising:
    a housing including:
        a main body portion having a closed proximate end and an open distal end with side walls extending between said proximate and distal ends defining a cavity between said closed proximate end and side walls; and
        a lower body portion having open proximate and distal ends defining a center passage between said proximate and distal ends with the proximate end of the lower body portion affixed to the distal end of said main body portion;
    an ultrasonic transducer captured within said closed proximate end of said main body portion; and
    a flexible membrane across said center passage of the lower body portion in close proximity to, and spaced-apart from said distal end of said lower body portion with said flexible membrane defining at least one hole therethrough;
    a first chamber is defined between said ultrasonic transducer and said flexible membrane and a second chamber is defined between said flexible membrane and the distal end of said lower body portion with said second chamber being substantially smaller than said first chamber, with each of said first and second chambers disposed to contain a liquid ultrasonic couplant;
    said main body portion defines a couplant input port through a side wall into said first chamber below said ultrasonic transducer disposed to input, and maintain, couplant in said first chamber and said at least one hole in said flexible membrane disposed to pass couplant therethrough to said second chamber from said first chamber; and
    said lower body portion defines, in said second chamber and in close proximity to said flexible membrane, at least one vacuum passage though a side wall of said center passage extending to, and through, an outer surface other than said distal end of said lower body portion with said vacuum passage disposed to be coupled to a vacuum source.

5. A miniature acoustic inspection device for a workpiece as in claim 4:
    wherein said at least one hole in said flexible membrane is substantially centered in said flexible membrane; and
    an inner side of said center passage of said lower body portion defines, in close proximity to said flexible membrane, a passage therethrough disposed to have a vacuum applied to an outside end of said passage;
    wherein when couplant flows into said second chamber through said at least one hole in said flexible membrane the centering of said at least one hole forces air bubbles contained in said couplant to said side wall of said center passage in close proximity to said flexible membrane when said inspection device is in place on a workpiece with said bubbles disposed to be drawn out of said second chamber through said passage when a vacuum is applied to said outside end of said passage.

6. The miniature acoustic inspection device for a workpiece as in claim 4 wherein:

said lower body portion further defines in the distal end thereof a vacuum chamber spaced apart from, and at least partially surrounding, said center passage and at least one vacuum path coupling said vacuum chamber to an outer surface other than said distal end of said lower body portion with said vacuum path disposed to be coupled to a vacuum source.

7. The miniature acoustic inspection device for a workpiece as in claim 4 wherein said lower body portion further defines in the distal end thereof a vacuum chamber spaced apart from, and at least partially surrounding, said center passage and at least one vacuum path coupling said vacuum chamber to an outer surface other than said distal end of said lower body portion with said vacuum path disposed to be coupled to a vacuum source and when said inspection device is in place on a workpiece and couplant is flowing into said second chamber through said at least one hole in said flexible membrane with a vacuum applied to said vacuum path which in turn is applied to said vacuum chamber, couplant is drawn from said second chamber under a portion of said distal end of said lower body portion between said second chamber and said vacuum chamber, into said vacuum chamber and out through said at least one vacuum path.

8. The miniature acoustic inspection device for a workpiece as in claim 4 wherein said lower body portion further defines in the distal end thereof a vacuum chamber spaced apart from, and at least partially surrounding, said center passage and at least one vacuum path coupling said vacuum chamber to an outer surface other than said distal end of said lower body portion with said vacuum path disposed to be coupled to a vacuum source wherein when said couplant is uncompressible, at least said portion of the distal end of said lower body portion under which said couplant is flowing is supported above said workpiece by said couplant.

9. The miniature acoustic inspection device for a workpiece as in claim 4 wherein said lower body portion further defines in the distal end thereof a vacuum chamber spaced apart from, and at least partially surrounding, said center passage and at least one vacuum path coupling said vacuum chamber to an outer surface other than said distal end of said lower body portion with said vacuum path disposed to be coupled to a vacuum source wherein when said workpiece surface has bubbles and/or debris thereon in a path of said couplant drawn to said vacuum chamber, said couplant sweeps said bubbles and/or debris to said vacuum chamber and out through said at least one vacuum path with said couplant as said inspection device is advanced along said workpiece.

* * * * *